(12) United States Patent
Grant

(10) Patent No.: US 11,516,392 B2
(45) Date of Patent: Nov. 29, 2022

(54) PRIVACY CONTROLS FOR IMPLANTED ELECTRONICS

(71) Applicant: Strathspey Crown, LLC, Newport Beach, CA (US)

(72) Inventor: Robert Edward Grant, Laguna Beach, CA (US)

(73) Assignee: Strathspey Crown, LLC, Newport Beach, CA (US)

( * ) Notice: Subject to any disclaimer, the term of this patent is extended or adjusted under 35 U.S.C. 154(b) by 207 days.

(21) Appl. No.: 17/103,564

(22) Filed: Nov. 24, 2020

(65) Prior Publication Data

US 2022/0166931 A1    May 26, 2022

(51) Int. Cl.
*H04N 5/232* (2006.01)
*A61F 9/08* (2006.01)
*G06F 9/54* (2006.01)
*G06V 20/10* (2022.01)

(52) U.S. Cl.
CPC ......... *H04N 5/232411* (2018.08); *A61F 9/08* (2013.01); *G06F 9/542* (2013.01); *G06V 20/10* (2022.01); *A61F 2250/0058* (2013.01)

(58) Field of Classification Search
CPC .............................................. H04N 5/232411
USPC ..................................................... 348/207.99
See application file for complete search history.

(56) References Cited

U.S. PATENT DOCUMENTS

| | | | |
|---|---|---|---|
| 4,955,904 A | 9/1990 | Atebara | |
| 7,001,427 B2 | 2/2006 | Aharoni et al. | |
| 9,101,279 B2 * | 8/2015 | Ritchey | ................ A61B 5/6803 |
| 9,662,199 B2 | 5/2017 | Grant | |
| 10,299,912 B2 | 5/2019 | Grant | |
| 10,904,376 B1 * | 1/2021 | Petri | ...................... G06Q 50/01 |
| 2010/0234942 A1 | 9/2010 | Peyman | |
| 2013/0194540 A1 | 8/2013 | Pugh et al. | |
| 2015/0002674 A1 * | 1/2015 | Kleve | ...................... H04N 7/18 348/149 |
| 2015/0182330 A1 * | 7/2015 | Grant | ..................... A61B 5/686 623/6.37 |
| 2017/0075414 A1 | 3/2017 | Grant et al. | |
| 2017/0336641 A1 | 11/2017 | von und zu Liechtenstein | |
| 2017/0337352 A1 * | 11/2017 | Williams | ................ G06F 21/10 |

FOREIGN PATENT DOCUMENTS

KR    20200076257    6/2020
WO    2006015315 A2    2/2006

OTHER PUBLICATIONS

International search report dated Mar. 18, 2022, for related PCT application No. PCT/US21/60879. 9 pages.

* cited by examiner

*Primary Examiner* — Joel W Fosselman
(74) *Attorney, Agent, or Firm* — Fish IP Law, LLP

(57) ABSTRACT

An implantable system includes an implanted camera that captures images. An analytics engine analyzes the images to determine whether any objects or aspects of the captured image is considered an unviewable element. Upon determining that an unviewable element is present, the analytics engine causes an occlusion device to occlude the unviewable element from the user's view. The occlusion can also affect the ability of the camera to continue to see the unviewable element.

6 Claims, 7 Drawing Sheets

PRIVACY CONTROLS FOR IMPLANTED ELECTRONICS

FIELD OF THE INVENTION

The field of the invention is implantable technologies.

BACKGROUND

The background description includes information that may be useful in understanding the present invention. It is not an admission that any of the information provided herein is prior art or relevant to the presently claimed invention, or that any publication specifically or implicitly referenced is prior art.

The emergence of implantable technologies has made possible what was once considered science fiction. Implantable cameras have enabled previously blind users to see, with ever-increasing fidelity.

Implantable displays, in turn, have opened up new areas of enhancing a user's access to information as they navigate the real world. The ability to access information without having to carry or wear a separate device allows for the seamless integration of augmented reality into a user's everyday experience.

However, this powerful new technology brings with it new security concerns. A person wearing an implanted camera cannot take it off in locations where photography is not permitted. Likewise, operators of a secure location will not know if a person coming into the area has the ability to record what they view. As such, the privacy and security of those around a user of implanted technology is potentially jeopardized without their knowledge or consent.

Thus, there is still a need for a system that balances the benefits of implanted technologies to the user with the privacy and security concerns of the world around them.

SUMMARY OF THE INVENTION

The inventive subject matter provides apparatus, systems and methods in which an analysis engine executed by one or more processors obtains image data (e.g., an image or a series of images) from a camera implanted in the eye of a user. The analysis engine then determines that at least a portion of the image contains at least a portion of an unviewable element. Based on this determination, the analysis engine causes an implanted device to occlude the visible portion of the unviewable element such that the user is no longer able to see that portion.

In embodiments of the inventive subject matter, the occlusion by the occluding device is altering the transparency of a see-through element of the occluding device such that the portion of the see-through element that aligns with the unviewable element is no longer see-through. This way, the unviewable element is unviewable from the perspective of the camera.

In embodiments of the inventive subject matter, the occlusion by the occluding device is overlaying graphics or other imagery over the unviewable element such that the unviewable element is not visible from the perspective of the camera. In a variation of these embodiments, the graphical element can include a message indicating that the unviewable element is designated as unviewable.

In embodiments of the inventive subject matter, the analysis engine recognizes and determines an object in an image as an unviewable element based on image recognition of objects within the image and matching them against a database of objects previously determined to be unviewable elements.

In embodiments of the inventive subject matter, the analysis engine recognizes an identification code embedded upon an object depicted in the image and based on a match of the code, determines that the object having the identification code is an unviewable object.

In embodiments of the inventive subject matter, the system performs occlusion by turning off the camera and/or disabling the recording functions such that the images captured by the camera are not saved or stored anywhere.

In embodiments of the inventive subject matter, the analysis engine determines whether an object in an image is an unviewable element based at least in part on the location of the user. In these embodiments, objects that would otherwise not be unviewable become unviewable within a pre-defined location or geofence.

Various objects, features, aspects and advantages of the inventive subject matter will become more apparent from the following detailed description of preferred embodiments, along with the accompanying drawing figures in which like numerals represent like components.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

DETAILED DESCRIPTION

Throughout the following discussion, numerous references will be made regarding servers, services, interfaces, engines, modules, clients, peers, portals, platforms, or other systems formed from computing devices. It should be appreciated that the use of such terms, is deemed to represent one or more computing devices having at least one processor (e.g., ASIC, FPGA, DSP, x86, ARM, ColdFire, GPU, multi-core processors, etc.) programmed to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
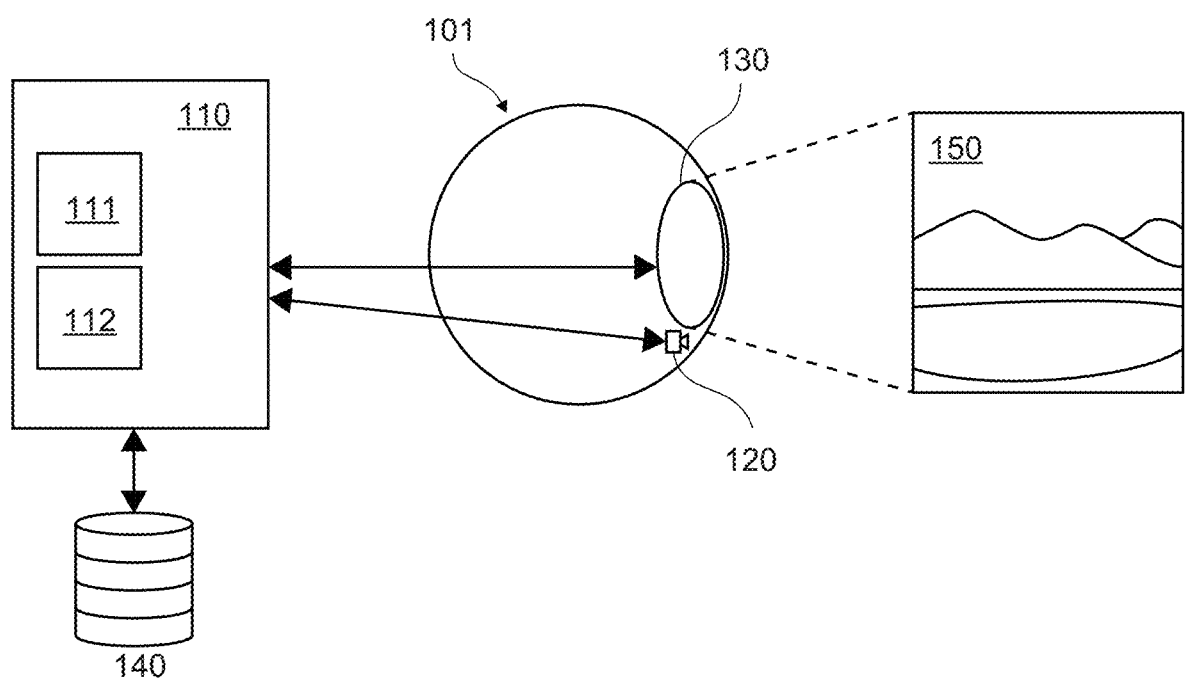
FIG. 1 is a diagrammatic overview of a system according to embodiments of the inventive subject matter.

FIG. 1 provides an overview of a system 100 according to embodiments of the inventive subject matter. The system 100 includes an analysis engine 110, a camera 120 and an occlusion device 130. As seen in FIG. 1, the system 100 can also include database 140 that stores images of unviewable elements (in some embodiments, as discussed below) or reference identification codes (in other embodiments, as discussed below) used to identify unviewable elements in the images.

Analytics engine 110 is made up of computer-executable instructions stored on a non-transitory computer readable medium that, when executed by one or more processors, carries out the functions described herein associated with the inventive subject matter. For the purposes of the examples discussed herein, recitations of "analytics engine 110" are considered to include the computing hardware (i.e., processor 111, non-transitory memory 112, and one or more data exchange interfaces) as well as the instructions themselves.

Camera 120 is implanted within the eye 101 of the user. Camera 120 is a forward-facing camera that captures images (such as scene 150) as seen from the perspective of the user. The images can be still images but are preferably video images captured as a live stream that represents the user's view in real-time or approximately real-time. The stream can be stored on a memory onboard the camera 120, occlusion device 130 or other memory implanted into the user's body. Alternatively, the video stream can be transmitted via wireless communication interfaces to a non-implanted memory on a separate computing device for storage.

In embodiments, analytics engine 110 can be implanted in the user's body, such as within the same eye 101 or elsewhere in the body. In some of these embodiments, the analytics engine 110 is part of the same implanted device with camera 120 and/or occlusion device 130. In other embodiments, the analytics engine 110 can be a separate computing device outside of the user's body that communicates with the camera 120 and the occlusion device 130 via a wireless data exchange interface.

Occlusion device 130 can be considered a display or other device implanted within the eye 101 that can allow for the obstruction of the user's view. The occlusion device 130 can be an augmented reality display implanted in the user's eye 101 that can be used for typical augmented reality functions. However, for the discussion here, this display is referred to as the occlusion device 130 to describe the functions of the display as applicable to the inventive subject matter.

As discussed in further detail in the embodiments below, an occlusion can be a graphical display and/or a change in the transparency of the occlusion device 130 (which can include a tinting or other change in transparency). In embodiments where the camera is behind the occlusion device 130, the occlusion device 130 can also affect the visible area of the camera 120 via an occlusion of the camera's visibility.

On example of a suitable implant that includes both a camera 120 and an occlusion device 130 are described in U.S. Pat. Nos. 9,662,199 and 10,299,912, both to Robert Grant. U.S. Pat. Nos. 9,662,199 and 10,299,912 are both incorporated by reference in their entirety.

US pre-grant patent publication 2017/0075414, also to Grant, describes an implantable/wearable device for detecting diverse anatomical/physiological data. WO 2006/015315 to Feldon describes a digital display positioned on an intraocular lens. US 2013/0194540 to Pugh describes antennas and antenna systems configured into ophthalmic devices, including contact lenses. US20100234942A1 (Peyman) describes intraocular lenses having pigment that can be adjusted automatically by the intensity of the external light, or by electrical stimulation. U.S. Pat. No. 7,001,427 to Aharoni, et al also discusses an intraocular display. These references are all incorporated by reference in their entirety.

Database 140 is shown as being separate from the analytics engine 110 in FIG. 1 (i.e., in another computing device communicatively coupled with the analytics engine 110). However, it is contemplated that the database 140 can be internal to the analytics engine 110, the camera 120 or the occlusion device 130.

Any of the system components that are implanted into the user can be powered by on-board batteries or any method of powering implanted devices known in the arts.

Figure 2:
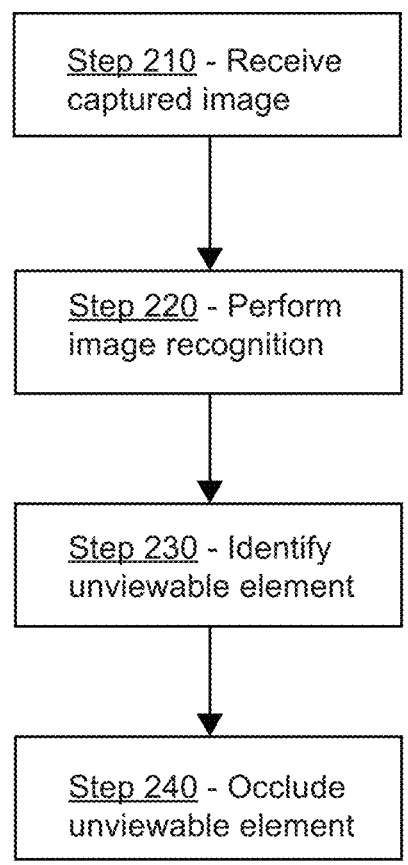
FIG. 2 is a flowchart illustrating a process of occluding an unviewable element, according to embodiments of the inventive subject matter.

FIG. 2 is a flowchart illustrating a process of occluding the view of the user according to embodiments of the inventive subject matter.

At step 210, the analytics engine 110 receives an image captured by camera 120. The image depicts at least a portion of an object or a scene 150. The image received can be a still image or a video image. In the embodiments discussed herein, the image is considered to be a continuous stream of video received from the camera 120 such that it represents a real-time or approximately real-time view of what the user is seeing.

Figure 3:
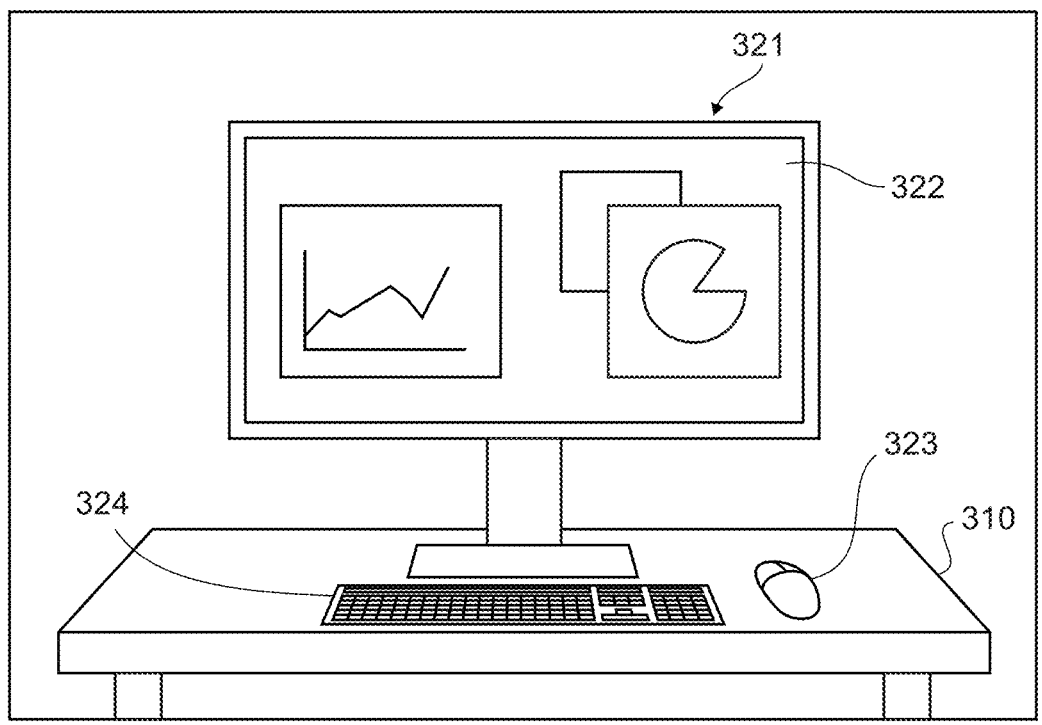
FIG. 3 is an example of a scene captured by a camera prior to any occlusions, according to embodiments of the inventive subject matter.

FIG. 3 is an example of an image captured by camera 120. The image of FIG. 3 depicts an office setting that includes a desk 310 and a computer 320. The computer 320 is shown to include a monitor 321 with a screen 322, a mouse 323 and a keyboard 324. As seen in FIG. 3, the screen 322 displays some information such as graphics that are visible with the naked eye and, without the methods and systems of the inventive subject matter, could be seen and recorded by camera 120.

At step 220, the analytics engine 110 performs image recognition on the received image to identify one or more objects within the image. The objects may be entirely in the image or partially in the image. To perform the image recognition, the analytics engine 110 can utilize one or more currently known or hereafter devised technique without departing from the scope of the invention.

In the example of FIG. 3, the analytics engine 110 performs image recognition and identifies the desk 310, monitor 321, screen 322, mouse 323 and keyboard 324.

At step 230, the analytics engine 110 determines whether any of the portions of the objects identified in the image correspond to an unviewable element.

An unviewable element is an object, part of an object, type of an object, or scene that has been a priori deemed unviewable. "Unviewable" for the purposes of the inventive subject matter means that it is intended that either the user's naked eye in which the camera 120 and occlusion device 130 are implanted, and/or camera 120 is prohibited from seeing the unviewable element (after the unviewable element has been discovered). or that the system 100 is prevented from recording/saving images where the unviewable element is visible. Examples of unviewable elements can include screens of certain designated computing devices, displays of content or types of content on screens or signage, documents (either individual documents or types of documents) designated as unviewable, certain imagery or types of imagery (e.g., imagery depicting violence, nudity, pornography, etc.).

The identification of an unviewable element within an image of step 230 can be performed via several methods. The following example embodiments can be used together or in the alternative and are not considered to be an exhaustive list of the possible methods of identifying an unviewable element.

For example, in an embodiment, the analysis engine 110 compares the objects identified in the image against a database of objects that have been designated as unviewable elements. If a match is found, the matching object in the received image is flagged by the analysis engine 110 as an unviewable element.

Figure 4:
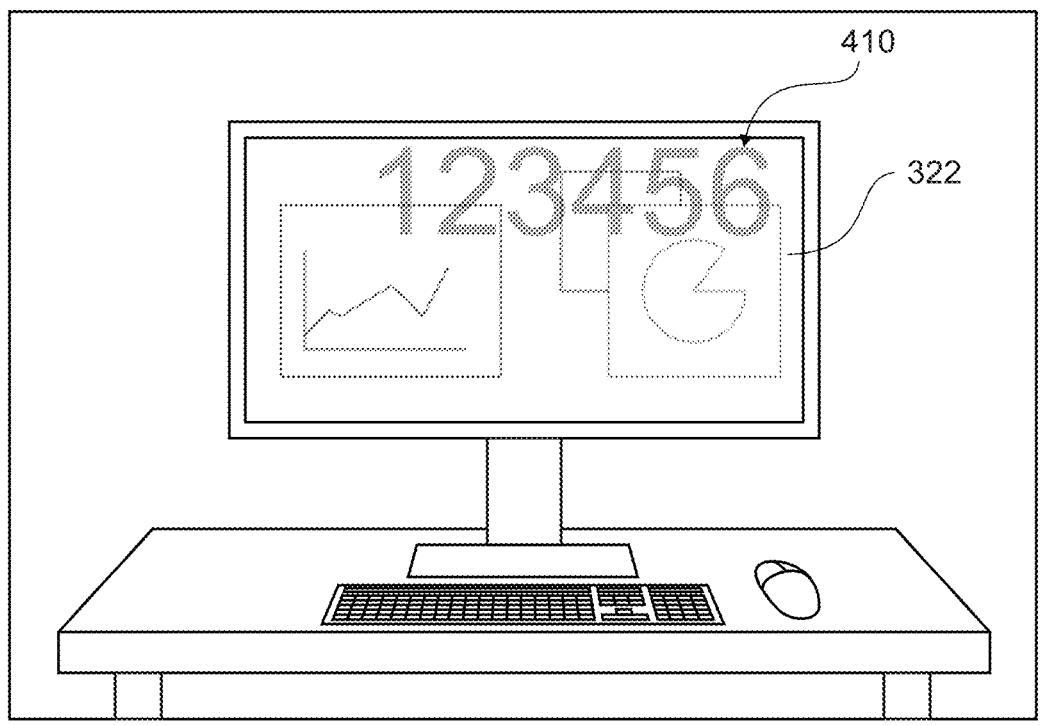
FIG. 4 provides an example of the scene of FIG. 3, with an identification code used to identify an unviewable element.

In another embodiment, the object in the image includes an identification code (e.g., a watermark, an alphanumeric code, a symbol, etc). The analysis engine 110 identifies the identification code disposed on the object and compares the identified identification against a database of identification codes corresponding to unviewable elements. If the analysis engine 110 finds a match, the object in the image bearing the identification code is flagged as an unviewable element. FIG. 4 illustrates this embodiment, showing a watermark 410 displayed on the screen 322.

It should be appreciated that the identification code 410 may or may not be visible or perceptible by the human user. For example, in certain embodiments the identification code 410 may be periodically presented only for one or more frames such that it is displayed too quickly for the human eye and brain to process, but that the system 100 can detect via the camera 120 and process accordingly. In other embodiments, the identification code 410 can be displayed at a wavelength of light and/or a brightness level such that it is functionally invisible to the user's naked eye but that can be captured and processed by the system 100.

In a variation of these embodiments, the analysis engine 110 is programmed to, prior to performing the image recognition at step 220, perform a scan of the image for potential identification codes (e.g., scan for alphanumeric codes of a certain length, format, or other recognizable type). Upon finding an identification code within the image, the analysis engine 110 the performs the image recognition at step 220. In these embodiments, the image recognition is limited to an area or region of the image proximate to the found identification code (e.g., the quarter or half of the image in which the identification code is located) to identify the object to which the identification code is affixed. In these embodiments, the identification of step 220 can be performed concurrent with or after the matching of the identification code to the plurality of identification codes in the database since the identification code match is used to determine the presence of an unviewable element in the image and not the identification of the object through image recognition.

In another embodiment, the analysis engine 110 determines whether an object within an image is an unviewable element at least in part on location information. The information location can be obtained from a separate device (e.g., a smartphone or computer) and received wirelessly. In embodiments, a device having a GPS radio or other location determination hardware can be implanted in the user (e.g., be a part of camera 120 and/or occluding device 130, or a separately implanted device). The location information associated with the user is then compared to a location (e.g., a geographical area) that has been designated as an area containing unviewable elements. Within that area, a certain object or type of object can be designated as an unviewable element. As such, any of the type of object will be deemed unviewable if identified as being visible within the designated area. For example, the implant device described in U.S. Pat. Nos. 9,662,199 and 10,299,912 (previously incorporated herein by reference) can include a GPS radio for position detection.

For example, in a company's research and development division, the system can be set such that all computer screens within the research and development department are considered unviewable elements. In this example, the analysis engine 110 determines that the user is within the research and development department by comparing the user's location to the designated area corresponding to the research and development department. If the images captured by the user's camera 120 within the research and development department include a computer screen, the analysis engine 110 is programmed to identify the computer screen and, because it is within the identified area, designate the computer screen as an unviewable element.

As step 240, the analysis engine 110 issues a command to occlusion device 130 to occlude the unviewable element identified at step 230. In response to the command, the occlusion device 130 occludes the unviewable element such that it is not visible by the user via the eye containing the occlusion device 130.

Figure 5:
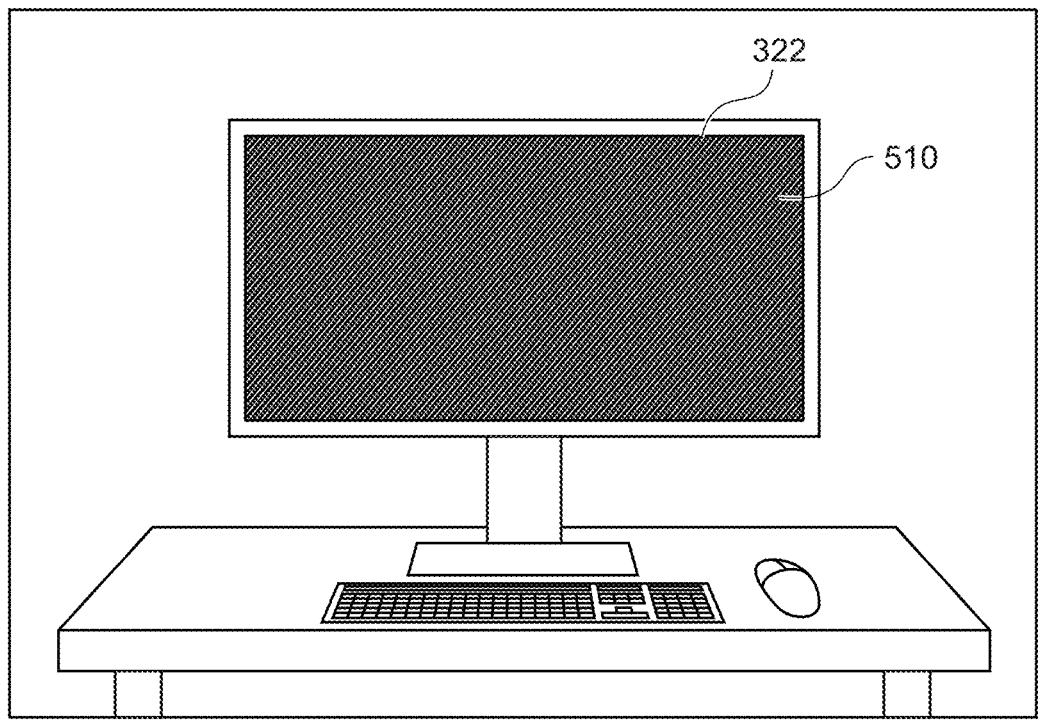
FIG. 5 provide an example of an occlusion using graphic elements, according to embodiments of the inventive subject matter.

Some examples of the occlusion performed by the occlusion device 130 include, but are not limited to:

In embodiments, the occlusion by the occlusion device 130 can comprise displaying graphics overlaying the unviewable element such that the unviewable element is either not visible or so that it is visibly unrecognizable by the user. This example is shown in FIG. 5, where the graphical pattern 510 obscures the images displayed on the screen 322.

Figure 6:
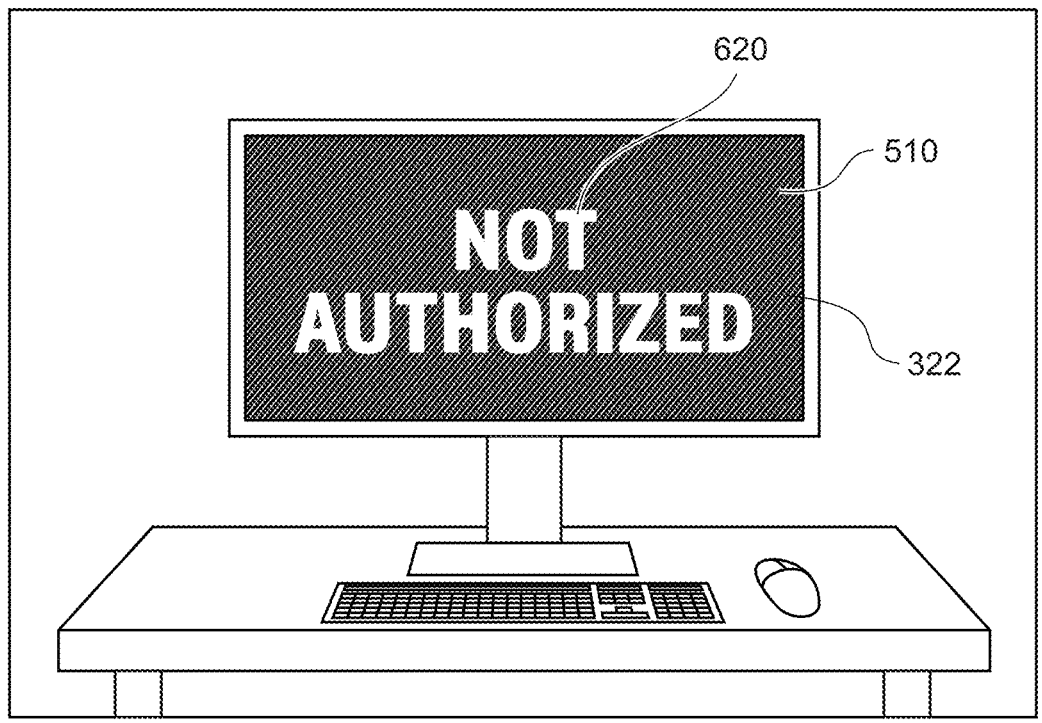
FIG. 6 provides an example of an occlusion that includes a message regarding the unviewable element, according to embodiments of the inventive subject matter.

In a variation of these embodiments seen in FIG. 6, the occlusion device 120 can include a message 620 displayed over the unviewable element on screen 322 in addition to graphics 510 such that the unviewable element is not visible to the user. These embodiments of the inventive subject matter can help inform the user why the element is not visible such that the user can take appropriate action to avoid the discomfort of having their vision partially blocked (e.g., look in a different direction). In the example of FIG. 6, the message simply says "Not Authorized." However, it is contemplated that the message can be a URL or QR code that leads to a website where user may input a password, upon which the user is authorized and the full vision restored by removing the graphics 510 and text 620.

Figure 7:
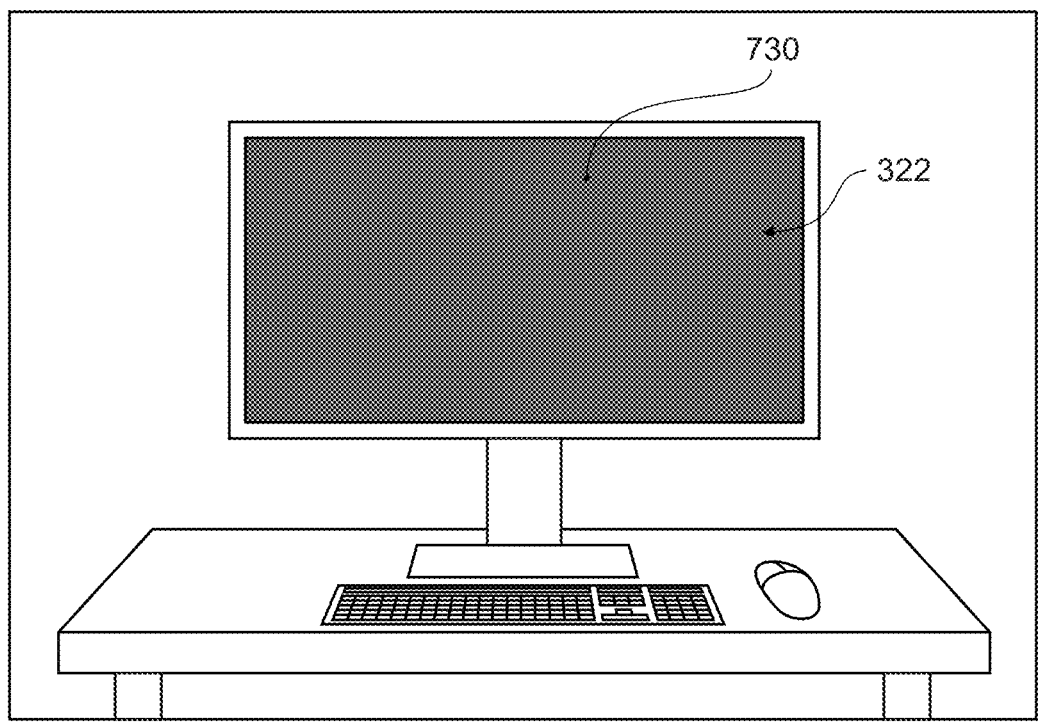
FIG. 7 provides an example of an occlusion in the form of a tinting occlusion, according to embodiments of the inventive subject matter.

In other embodiments, the occlusion by the occlusion device 120 can include altering the transparency of the visible field through the occlusion device 120 such that the unviewable element is not visible or otherwise unrecognizable by the user. In a variation of these embodiments, the change of transparency by the occlusion device 120 can include a tinting of the display area overlaying the unviewable element such that the unviewable element is not visible or otherwise unrecognizable by the user from the perspective of the camera. FIG. 7 provides an illustration of this embodiment, where tinting 730 is overlaid over the screen 322 such that the content within screen 322 is not visible to the user.

As the camera 120 continues to stream video to the analysis engine 110, the analysis engine 110 continuously repeats the process of steps 210-240 such that an unviewable element can be tracked as it moves through the camera's field of view and such that the occlusion device 130 occludes in the corresponding location of the unviewable element within the user's field of view.

As noted above, in certain embodiments the camera 120 is implanted within the eye such that it is behind the screen that serves as the occlusion device 130. In these embodiments, the occlusions that block portions of the user's vision relative to unviewable elements also serve to block the camera's view of the same unviewable elements.

In embodiments where the camera 120 cannot be obstructed by the occlusion device 130, the analytics engine 110 can instead apply image editing techniques to the recorded video signal such that the occlusions created by the occlusion device 130 are mirrored in the recorded video signal.

It should be noted that if the implantable camera is only implanted in one eye, the user will still be able to see the unviewable element through the other eye. However, the systems and methods of the inventive subject matter prevent the unauthorized or undesired recording by the implanted camera of the unviewable elements. As such, for example, a user might be able to see a live performance but not record it for later viewing or distribution.

In embodiments, the analytics engine 110 can, in response to identifying an unviewable object, issue a command to the camera 120 to power off or to stop recording. In these embodiments, the powering off can be for a particular period of time after which the camera 120 turns back on to take a sample image. If the analytics engine 110 finds that the unviewable element remains (or a new unviewable element is found), it sends a new command to the camera 120 to power down or stop recording for another period of time.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of occluding vision using an implanted device, comprising:

receiving, by an analytics engine, an image captured by a camera implanted within an eye of a user;

determining, by the analytics engine, that the image contains at least a portion of an unviewable element; and occluding, by an implanted occlusion device, the at least a portion of the unviewable element such that the at least a portion of the unviewable element is not visible to the user, wherein occluding further comprises altering a transparency of a section of a see-through element such that the altered transparency obscures the unviewable element;

overlaying, by the implanted occlusion device, a message over the altered section of transparency that indicates the unviewable element is unviewable.

2. The method of claim 1, wherein the determining step further comprises:

recognizing, by the analytics engine, an object within the image by applying at least one image recognition technique;

comparing, by the analytics engine, the recognized object with a plurality of unviewable elements stored in a database;

determining a match between the recognized object and at least one of the plurality of unviewable elements; and flagging, by the analytics engine, the matching recognized object as the at least a portion of the unviewable element.

3. The method of claim 1, wherein the determining step further comprises:

recognizing, by the analytics engine, an identification code disposed on an object within the image;

comparing, by the analytics engine, the identification code with a plurality of unviewable element codes stored within a database;

determining, by the analytics engine, a match between the recognized identification code and an unviewable element code from the plurality of unviewable element codes; and flagging, by the analytics engine, the object as the at least a portion of the unviewable element.

4. The method of claim 1, wherein the step of determining is based at least in part on a location of the user.

5. The method of claim 1, wherein altering a transparency of a see-through element such that the altered transparency obscures the unviewable element further comprises changing a tinting of the see-through element.

6. The method of claim 1, further comprising:

in response to occluding the unviewable element, providing access to a password-entry interface;

receiving a password via the password-entry interface;

authorizing the user based on the password; and in response to authorizing, removing the occlusion.

* * * * *